US005767130A

United States Patent [19]
Olney

[11] Patent Number: 5,767,130
[45] Date of Patent: Jun. 16, 1998

[54] USE OF KAINIC ACID ANTAGONISTS TO PREVENT TOXIC SIDE EFFECTS OF NMDA ANTAGONISTS

[76] Inventor: John W. Olney, 1 Lorenzo La., St. Louis, Mo. 63124

[21] Appl. No.: 407,068

[22] Filed: Mar. 20, 1995

Related U.S. Application Data

[63] Continuation-in-part of Ser. No. 877,839, May 1, 1992, which is a continuation-in-part of Ser. No. 467,139, Jan. 18, 1990, abandoned, which is a continuation-in-part of Ser. No. 424,548, Oct. 20, 1989, Pat. No. 5,034,400.

[51] Int. Cl.⁶ .......... A61K 31/445; A61K 31/54; A61K 31/44; A61K 31/135
[52] U.S. Cl. .......... 514/315; 514/226.2; 514/280; 514/282; 514/318; 514/646
[58] Field of Search .......... 514/315, 226.2, 514/318, 646, 282, 280

*Primary Examiner*—Kevin E. Weddington
*Attorney, Agent, or Firm*—Patrick D. Kelly

[57] ABSTRACT

This invention discloses that kainic acid receptor antagonists (KA antagonists) can act as "safener" agents to reduce or prevent adverse side effects caused by NMDA antagonists. NMDA antagonists can reduce excitotoxic brain damage due to stroke, cardiac arrest, asphyxia, etc., but they also cause toxic damage to certain types of neurons, as well as psychotomimetic effects such as hallucinations. Co-administration of a KA antagonist can (1) reduce or prevent such undesired side effects, and (2) increase the extent of neuronal protection provided to the CNS, beyond the levels of protection that can be provided by NMDA antagonists alone, or non-NMDA antagonists alone. Therefore, co-administration of a KA antagonist allows NMDA antagonists to be used more safely and effectively.

16 Claims, 1 Drawing Sheet

1

USE OF KAINIC ACID ANTAGONISTS TO PREVENT TOXIC SIDE EFFECTS OF NMDA ANTAGONISTS

RELATED APPLICATION

This application is a continuation-in-part of U.S. patent application Ser. No. 07/877,839, filed on May 1, 1992, which was a continuation-in-part of U.S. application Ser. No. 07/467,139, filed on Jan. 18, 1990, now abandoned, which was a continuation-in-part of U.S. application Ser. No. 07/424,548, filed on Oct. 20, 1989, which issued as U.S. Pat. No. 5,034,400.

BACKGROUND OF THE INVENTION

The present invention is in the fields of neurology and pharmacology, and pertains to methods and preparations for treating or preventing toxic side effects of drugs that block neuronal receptors referred to as NMDA receptors.

Background information on the glutamate transmitter system and on NMDA glutamate receptors is provided in a number of reference works, including Choi 1988 and Olney 1989 (full citations are provided below). The most relevant features of this information are summarized in the following paragraphs.

The Glutamate Neurotransmitter System

Glutamate (the ionized form of glutamic acid, an amino acid; abbreviated as Glu) is recognized as the predominant excitatory neurotransmitter (messenger molecule) in the central nervous system (CNS) of all mammals. For a review, see the chapter by Olney, entitled "Glutamate," in *The Encyclopedia of Neuroscience* (1987 or 1995 editions). Glu is involved in transmitting messages from one nerve cell (neuron) to another in many different circuits within the CNS that serve many important functions. Glu mediates these functions by being released from a transmitting neuron, into a synapse (a signal-transmitting junction between two neurons). Immediately after entering the synaptic fluid that fills the synapse, the Glu contacts and briefly binds to a response at a synapse, the Glu contacts and briefly binds to a response at a receptor molecule on the surface of a receiving neuron. Binding of Glu to the synaptic receptor initiates signal transfer by causing the opening of an ion channel which allows ionic current flow across the membrane of the neuron, thereby altering its chemical state. This is considered an excitatory process, because it stimulates an increased level of electrochemical activity in the receiving neuron.

Glutamate Receptor Types: NMDA, KA, and QUIS/AMPA

There are several different subtypes of receptors through which Glu transmits messages. A particularly important receptor through which Glu mediates a wide range of functions is the N-methyl-D-aspartate (NMDA) receptor, which is so called because NMDA, a molecule structurally related to Glu, is highly selective and potent in activating this receptor.

The two other major classes of Glu receptors are (1) kainic acid (KA) receptors and (2) a type of receptor which was initially called the QUIS receptor, since it is activated by quisqualic acid. To avoid confusion by a different metabotropic receptor, which is also triggered by quisqualic acid, this receptor is now usually called the AMPA receptor (AMPA stands for alpha-amino-3-hydroxy-5-methylisoxazole-4-propionic acid). The AMPA designation is becoming the standard designation, and many so-called "non-NMDA" antagonists are now referred to simply as AMPA antagonists. However, since many articles and patents refer to this receptor as the QUIS receptor, it is referred to herein as the QUIS/AMPA receptor.

KA receptors and QUIS/AMPA receptors are often referred to collectively as "non-NMDA" receptors, and they share a substantially higher level of cross-affinity with various ligands than either class shares with NMDA receptors.

All drugs which have been announced to date which bind to either type of non-NMDA receptor also bind to the other type. Therefore, in the literature, such drugs usually are referred to collectively as non-NMDA receptor antagonists. However, the Applicant has recently discovered (and this patent application discloses) an important functional distinction between KA receptors, and QUIS/AMPA receptors. In specific, the Applicant has discovered that KA receptors, but apparently not QUIS/AMPA receptors, are located on the surfaces of the PC/RS pyramidal neurons which are damaged by the toxic side effects of NMDA antagonists. Accordingly, this patent application uses the term, "KA antagonists" to refer to drugs which suppress excitatory activity at KA receptors, regardless of whether they also suppress activity at QUIS/AMPA receptors.

All three classes of receptors (NMDA, KA, and QUIS/AMPA) are normally activated by glutamate, and are most commonly referred to as glutamate (or Glu) receptors. They are also activated, to a lesser extent, by aspartate, a related excitatory amino acid; accordingly, Glu receptors are also sometimes referred to as "excitatory amino acid" (EAA) receptors.

Antagonist Drugs that Block NMDA Receptors

As will be described below, drugs called "NMDA antagonists" (i.e., drugs that block or reduce the excitatory activities of glutamate and aspartate at NMDA receptors) offer great promise as therapeutic agents, and a number of drug companies have recently been developing several classes of such drugs. One class, referred to as competitive antagonists, bind at the NMDA/GLU binding site; such drugs include CPP, D-CPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Other drugs, referred to as non-competitive NMDA antagonists, bind at other sites in the NMDA receptor complex; such drugs include phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L689,560, L-687,414, ACPC, ACPCM, ACPCE, arcaine, diethylenetriamine, 1,10-diaminodecane, 1,12-diaminododecane, ifenprodil, and SL-82.0715. For reviews, citations, and complete chemical formulas for these compounds, see, e.g., Boast 1988, Rogawski 1992, Massieu et al 1993, and other articles cited therein, and U.S. Pat. No. 5,124,319 (Baudy et al 1992).

One NMDA antagonist that deserves particular note is MK801, developed by Merck Company. It is the maleate salt of dizocilpine, and is widely used by researchers since it is one of the most selective and powerful NMDA antagonists ever discovered. It operates as a non-competitive antagonist by triggering the PCP binding site.

Antagonist Drugs that Block KA and QUIS/AMPA Receptors

As noted above, all drugs which have been discovered and announced thus far which block either KA receptors or QUIS/AMPA receptors have been found to block both of these non-NMDA receptor subtypes. Accordingly, such drugs are usually referred to as non-NMDA antagonists.

For several years, efforts to develop non-NMDA antagonists lagged behind the development of NMDA antagonists. However, in recent years, several promising non-NMDA antagonists which can penetrate the mammalian blood-brain barrier and selectively suppress activity at non-NMDA receptors (i.e., with affinities for non-NMDA receptors at least about 3 times higher than their affinities for NMDA receptors) have been developed and announced in various patents, scientific conferences, and articles. This field of research is receiving strong attention by several major pharmaceutical companies, and in addition to the various non-NMDA antagonists that have been publicly announced, a number of additional not-yet-announced non-NMDA antagonists are approaching publication and/or formal requests for governmental approvals to allow clinical testing in humans.

The first drug that was identified as a non-NMDA antagonist was kynurenic acid. This drug was useful in research, but it had no therapeutic application in the CNS because it is a very weak non-NMDA antagonist, and it does not penetrate blood brain barriers. In addition, its blocking activity at non-NMDA receptors is not very selective, i.e., it blocks both NMDA and non-NMDA receptors. In fact, kynurenic acid is substantially more potent in blocking NMDA receptors, than non-NMDA receptors.

The next agents that were developed as non-NMDA antagonists were halogenated derivatives of kynurenic acid (e.g., 7-chlorokynurenic acid, 5,7-dichlorokynurenic acid, and 5-iodo-7-chlorokynurenic acid). These agents were more potent than kynurenic acid, but they had the same disadvantages as kynurenic acid (they were not selective for non-NMDA receptors, and they failed to penetrate the blood-brain barrier).

The next generation of non-NMDA antagonists were a family of compounds called quinoxalinediones. The first two agents announced in this category were CNQX (6-cyano-7-nitroquinoxaline-2,3-dione) and DNQX (6,7-dinitro-quinoxaline-2,3-dione); see Honore et al 1987 and 1988. Both of these agents were an improvement over prior compounds in that, although they blocked both NMDA and non-NMDA receptors, they were substantially more potent in blocking non-NMDA receptors than NMDA receptors. However, these agents were subject to two major limitations: they were not very soluble in aqueous solution, and they could not penetrate blood-brain barriers.

Nevertheless, as the most highly selective non-NMDA antagonists available, CNQX and DNQX were useful in certain types of research, and the Applicant used CNQX to demonstrate an important principle regarding neuroprotection against ischemic neuronal degeneration. Initially using embryonic chick retina tissue tests (described in Example 1), and subsequently using an in vivo adult mammalian model of ischemia (described in Example 2), the Applicant showed that a powerful NMDA antagonist, MK-801, was able to provide a maximum of only about 40% protection against ischemic neuronal degeneration, and the non-NMDA antagonist CNQX was able to provide a maximum of only approximately 35–40% protection. However, if these two agents were combined together it was possible to obtain more than 80% protection. In the in vivo assays, the fact that CNQX did not penetrate blood brain barriers was not a problem, because CNQX was injected into the vitreous fluid inside the eye, which permitted the CNQX to directly contact the ischemic retinal tissue.

These findings signified that both NMDA and non-NMDA Glu receptors participate in the processes that lead to ischemic neuronal degeneration in the mammalian CNS, and that in order to obtain maximal and optimal protection against excitotoxic damage to CNS neurons, it is necessary to use drugs that suppress activity at both NMDA receptors, and non-NMDA receptors. After making that discovery, the Applicant filed an above-cited related parent application (U.S. patent application Ser. No. 07/467,139), in January 1990. It was subsequently abandoned and superseded by U.S. patent application Ser. No. 07/877,839, filed in May 1992.

The next major step forward in the development of drugs that can selectively block activity at non-NMDA receptors was NBQX (2,3-dihydroxy-6-nitro-7-sulfamoyl-benzo(F) quinoxaline), described in PCT application WO-92/11012 (invented by T. Klockgether et al, assigned to Schering Berlin & Bergkamen AG) and in Sheardown et al 1990. This compound was an important improvement over CNQX and DNQX, because it penetrated bloodbrain barriers in appreciable quantities.

The Applicant obtained a sample of NBQX (a gift from Novo-Nordisk, the company that developed NBQX) and performed experiments using the above-mentioned adult rat retina model, in which NBQX was substituted for CNQX. The same results were obtained, i.e., it was shown that either a NMDA antagonist or a non-NMDA antagonist could provide a maximum of only about 40% protection against ischemic retinal degeneration, but a combination of the two drugs provided more than 80% protection.

In addition, other researchers tested NBQX as a neuroprotective agent in various models of cerebral ischemia, and reported that NBQX provided protection which, in some respects, was better than had been reported for any NMDA antagonists. For example, NMDA antagonists consistently provided significant protection against neuronal degeneration in animal models of focal cerebral ischemia (which simulate strokes in which blood supply to only a portion of the brain is disrupted), but provided only equivocal or no protection in models of global ischemia (which involve cessation of blood supply to the entire brain, as occurs during cardiac arrest). Moreover, NMDA antagonists provided best protection when administered very soon after the ischemic insult, and were relatively ineffective if not administered until after a delay of several hours. In contrast, NBQX apparently provided significant protection in both focal and global ischemia, and conferred protection even when not administered until several hours after the ischemic event.

Despite these very favorable results, NBQX suffered from two major limitations. First, its duration of action in the CNS is very brief (only about 15 min or less), since it is metabolized and cleared from the blood circulation very rapidly. And second, the aqueous solubility of NBQX is very limited, which led to various problems such as nephrotoxicity.

Several pharmaceutical companies have been working to overcome these problems, and a new generation of post-NBQX non-NMDA antagonists have been publicly described in various patents and published patent applications. Some of the most promising compounds are third-generation (post-NBQX) quinoxalinediones that have arisen out of a research partnership between Novo-Nordisk, a Danish firm, and Schering AG, in Berlin. These compounds are described in PCT applications WO-94/25469 (invented by A. Huth and L. Turski), WO-94/25470 (invented by P. Holscher et al), and WO-94/25472 (invented by M. Kruger et al), which are assigned to Schering AG, and in PCT applications WO-93/06103 and WO-94/21639 (invented by P. Jacobsen et al), assigned to Novo-Nordisk AS. The non-NMDA antagonists described in these applications are believed to avoid the solubility limitations and nephrotoxicity problems of NBQX.

In addition, Merck, Sharp & Dohme, Ltd. has obtained or applied for British patents 2,266,888 (hydroxy-pyrrolone derivatives) and 2,265,372 (hydroxy-pyrrolo-pyridazinone derivatives), invented by J. J. Kulagowski et al; U.S. Pat. Nos. 5,376,748 (nitroquinolone derivatives) and 5,252,584 (hydroxyquinolones), invented by W. R. Carling et al; U.S. Pat. No. 5,348,962 (aryl-hydroxy-quinolone derivatives), invented by J. J. Kulagowski et al; U.S. Pat. No. 5,268,378 (dioxo-tetrahydroquinoline derivatives), invented by R. Baker et al; and PCT applications WO-93/10783 (quinolones) and WO-93/11115 (aryl substituted quinolones), invented by W. R. Carling et al.

Nova Pharmaceutical Corporation has applied for PCT application WO-93/05772 (omega-phosphonoalkyl-phenyl-amino alkanoic acid derivatives), invented by S. R. Ellenberger et al.

Yamanouchi Pharmaceutical Company Ltd. has applied for PCT applications WO-93/20077 (fused quinoxalinone derivatives) and WO-92/07847 (fused pyrazine derivatives), both invented by K. Hidaka et al.

Warner Lambert Company has obtained U.S. Pat. No. 5,192,792 (isatin derivatives), invented by G. Johnson, and has applied for PCT application WO-93/04688 (uricosuric agents), invented by C. F. Bigge et al.

Guilford Pharmaceuticals, Inc. has obtained U.S. Pat. Nos. 5,342,946 (phosphono-alkyl-quinolinone compounds) and 5,364,876 (amino-phenyl(alkyl)-acetic acid derivatives), both invented by G. S. Hamilton.

Rhone Poulenc Rorer SA has applied for PCT application WO-93/21171 (benzothiadiazine carboxylic acid derivatives), invented by J. Aloup et al.

Adir & Cie, a French company, has published European patent application 618209 (pyrido-thiadiazine-dioxides), invented by P. De Tullio et al.

In addition, a non-NMDA antagonist designated as GYKI 52466 (described in Tarnawa et al 1990), developed in Hungary, has been shown to exert non-competitive blocking action at non-NMDA receptors and appears to be highly selective for nonNMDA receptors, i.e., it exerts no significant blocking activity at NMDA receptors. It is believed by the Applicant, based upon correspondence with the inventor of GYKI 52466, that this family of compounds has been licensed to a major pharmaceutical company, which is actively pursuing analogs and derivatives that have higher potency.

It should also be noted that a number of these compounds are reported or believed to have significant levels of antagonist activity at NMDA receptors, as well as at non-NMDA receptors.

Toxic Effects of Excessive NMDA Activity

Despite its role as a beneficial and absolutely essential neurotransmitter in healthy tissue, the Glu molecule can become a treacherous and deadly neurotoxin under certain conditions. Glu neurotoxicity is referred to as "excitotoxicity" because the neurotoxic action of Glu, like its beneficial actions, is mediated by an excitatory process (reviewed by Olney 1990 and Choi 1992).

Ordinarily, when Glu is released by a transmitting neuron into a synaptic junction, it binds only very briefly to a Glu receptor, then it is rapidly removed from the receptor region and the synaptic junction by a transport process that returns Glu back into a cell interior. Under certain abnormal conditions (including stroke, certain types of epilepsy, and CNS trauma), the Glu uptake process can fail, and Glu can begin to accumulate in synaptic junctions. This unnatural accumulation allows Glu to persistently excite electrochemical activity and cellular depolarization in the receptor-bearing neurons, until neurons that have Glu receptors are excited to a point where they deplete their cellular resources and die of overstimulation. Since almost all of the neurons in the CNS have Glu receptors, this mechanism can cause severe and widespread brain damage following acute CNS injury, including brain damage and neuronal death in regions that were not directly injured by the stroke or trauma.

As used herein, the term "acute CNS injury" includes ischemic events (which involve inadequate blood flow, such as a stroke or cardiac arrest), hypoxic events (involving inadequate oxygen supply, such as drowning, asphyxiation, or carbon monoxide poisoning), trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as the receptor subtype through which Glu mediates much of this acute CNS injury, and it is well-established that NMDA antagonists can be effective in protecting CNS neurons against excitotoxic degeneration in these acute CNS injury syndromes (reviewed by Choi 1988 and Olney 1990).

CNS trauma represents a special situation in which excessive activity at NMDA receptors can cause neuronal damage by both direct and indirect mechanisms. Persistent activation of NMDA receptors can directly excite neurons to death, but that is not the only risk. In addition, the hyperexcitation process involves excessive influx of charged ions into CNS cells, which creates an osmotic imbalance that causes abnormal amounts of water to flow in with the ions. This can result in excessive swelling of millions of CNS cells, causing increased intracranial pressure because the skull is inflexible and cannot expand to accommodate the increased volume of the swollen cells. Among other effects, elevated intracranial pressure tends to squeeze arteries and veins, causing even more reduction in their ability to carry fresh oxygenated blood to the brain. Through this and other mechanisms, elevated intracranial pressure contributes substantially to both morbidity and mortality in CNS trauma victims. Accordingly, NMDA antagonists are useful both in preventing or reducing direct excitotoxic damage, and in preventing or reducing damage caused by increased intracranial pressure.

In addition to neuronal damage caused by acute insults, excessive activation of Glu receptors may also contribute to more gradual neurodegenerative processes leading to cell death in various chronic neurodegenerative diseases, including Alzheimer's disease, amyotrophic lateral sclerosis (Lou Gehrig's disease), AIDS dementia, Parkinson's disease, and Huntington's chorea (Olney 1990). It is considered likely that NMDA antagonists will prove useful in the therapeutic management of such chronic diseases.

Excessive activation of NMDA receptors is also responsible for the generation of "neuropathic" pain, a type of pain which is sometimes called "neurogenic pain" or "wind-up" pain (Woolf et al 1989; Kristensen et al 1992; Yamamoto and Yaksh 1992). Neuropathic pain is a chronic condition in which NMDA receptors in neural pain pathways have become "kindled" to an abnormally high level of sensitivity so that they spontaneously convey nerve messages that the patient perceives as pain even though no painful stimulus has been inflicted. By mechanisms that are poorly understood, pathological changes associated with diabetes are conducive to the generation of neuropathic pain, a condition known as "diabetic neuropathy". One of the distinguishing characteristics of neuropathic pain is that morphine and related pain-killing drugs which are effective in controlling other types of pain are usually ineffective in controlling neuropathic pain (Backonja 1994). Several recent reports indicate that NMDA antagonists can prevent or ameliorate neuropathic pain (Davar et al 1991; Mao et al 1992; Seltzer et al 1991; Neugebauer et al 1993; Kristensen et al 1992; Backonja et al 1994).

NMDA receptor activation has also been implicated as a mechanism underlying the development of tolerance to various potentially addictive drugs. "Tolerance" is used broadly herein, to include any or all of the following: dosage-type tolerance to a drug, which implies that a person must take an increasing amount of a drug in order to achieve the same level of comfort or therapeutic benefit; dependence upon a drug, which implies that a patient must continue taking a drug to avoid withdrawal symptoms; and, craving for a drug, which can include physiological and/or psychological cravings. A number of recent reports indicate that in animal studies, NMDA antagonists apparently prevented the development of tolerance to opiate analgesics (Marek et al 1991; Trujillo and Akil 1991; Ben-Eliyahu et al 1992; Tal and Bennett 1993) or benzodiazepine anxiolytics (L. Turski et al, PCT patent application WO 94/01094). It has also been reported that ibogaine, a drug which the Applicant has recently shown to have NMDA antagonist properties, can suppress the craving for cocaine (e.g., Sershen 1994).

NMDA Antagonist Drugs: Both Beneficial and Detrimental

Since excessive excitatory activity by Glu can cause several types of neuronal damage or undesired effects, NMDA antagonists which can suppress glutamate activity at the NMDA class of Glu receptors have several important beneficial potentials. However, despite these beneficial potentials, NMDA antagonists can also cause serious detrimental neurotoxic side effects which manifest as pathomorphological changes in CNS neurons, and as psychotomimetic symptoms.

As described in Olney et al 1989b and U.S. Pat. No. 5,034,400 (Olney 1991), the pathomorphological damage caused by NMDA antagonists include the formation of vacuoles and the dissolution of mitochondria in various types of neurons. Since this type of cellular damage occurs in a reliable and detectable manner in neurons in the posterior cingulate and retrosplenial (PC/RS) regions of the cerebral cortex, those regions have been used for cellular evaluation in the tests described herein. These changes can be detected histologically within 2 to 4 hours following a single subcutaneous treatment using either competitive or non-competitive NMDA antagonists (Olney et al. 1991). Twenty four hours after NMDA antagonist treatment, the vacuolar changes are diminished, but other changes in the form of abnormal expression of heat shock protein (HSP) appear and remain detectable for up to 2 weeks after NMDA antagonist treatment. While all of the above changes occur following treatment with a relatively low dose of an NMDA antagonist, higher doses have been shown to kill neurons not only in the PC/RS cortex but in several other neocortical and limbic brain regions (Corso et al 1994; Fix et al 1993). In addition, it has been shown that subchronic treatment with daily injections of an NMDA antagonist for 3–5 days causes neuronal cell death in the PC/RS and other cortical and limbic brain regions (Corso et al 1992; Ellison and Switzer 1992; Horvath and Buzsaki 1993; Ellison 1995). It has been shown that both competitive and non-competitive NMDA antagonists cause both the vacuolar reaction and death of cerebrocortical neurons.

In addition to these pathomorphological changes, which can be objectively measured in the brains of laboratory animals, NMDA antagonists are also known to cause psychotomimetic effects in adult humans (reviewed by McCarthy 1981, and in Olney and Farber 1995). These psychotomimetic effects were first observed many years ago in patients treated with phencyclidine, a drug that was introduced into human medicine as an anesthetic in the late 1950s. This was long before it was known that phencyclidine acts as an NMDA antagonist, or before NMDA receptors were first described. In this early period, phencyclidine was introduced as an anesthetic agent and it was found immediately that patients anesthetized with phencyclidine displayed psychotic symptoms (termed an "emergence reaction") when they were coming out from under the anesthesia. Because these psychotomimetic side effects were quite severe, phencyclidine was immediately withdrawn from use in clinical medicine. Subsequently, phencyclidine became well known as a widely abused illicit hallucinogenic drug (often called angel dust or PCP).

In the 1980's, it was discovered that the site of action of PCP in the CNS is at a "PCP recognition site" within the ion channel of the NMDA receptor. At this site, PCP acts as a non-competitive antagonist that blocks the flow of ions through the NMDA ion channel. Thus, PCP and other agents which act at the PCP binding site (such as ketamine, tiletamine, and MK-801 (dizocilpine maleate)) became known as non-competitive NMDA antagonists. Since ketamine, a drug currently used in human anesthesia, is known to cause "emergence reactions" similar to but not as severe as those caused by PCP, it became evident to researchers in the late 1980's that all drugs acting at the PCP site as non-competitive NMDA antagonists were likely to have psychotomimetic side effects.

This caused some researchers to shift their focus away from non-competitive agents acting at the PCP site, and they began studying competitive NMDA antagonists acting at the NMDA recognition site. However, in the last few years three competitive NMDA antagonists (CPP, CPPene, CGS 19755) have been administered in relatively low doses to adult human subjects in clinical trials, and all three of these agents induced a psychotomimetic reaction. Therefore, it is now believed that various and apparently all competitive or non-competitive NMDA antagonists cause the same pathomorphological effects in rat brain (Olney et al 1991; Hargreaves et al 1993) and have psychotomimetic effects in humans (Kristensen et al 1992; Herrling 1994; Grotta 1994). Thus, it seems likely that these two types of side effects are morphological and psychological manifestations of the same toxic process and that the ability of a given agent to produce these adverse effects does not depend on the site within the NMDA receptor channel complex where it binds, but on the efficacy with which it blocks the functional activity of the NMDA receptor channel complex.

Therefore, in practical terms, a major obstacle to the use of NMDA antagonists as useful neurotherapeutic drugs lies in the fact that they cause adverse and potentially severe side effects, including psychotic reactions as well as neuronal death and permanent brain damage.

Safener Agents for Preventing Adverse Side Effects of NMDA Antagonist Drugs

It has been discovered by the Applicants that several types of drugs can act as "safener" agents to reduce or prevent the pathomorphological changes induced in rat brain by NMDA antagonists. Safener drugs previously described by the Applicants include several different classes:

(1) anticholinergic drugs which block the muscarinic class of cholinergic receptors, such as scopolamine, atropine, benztropine, trihexyphenidyl, biperiden, procyclidine, benactyzine or diphenhydramine; see Olney et al 1991, and U.S. Pat. No. 5,034,400 (Olney 1991);

(2) certain types of barbiturates, such as secobarbitol (Olney et al 1991), which interact with various neuronal receptors, including Glu receptors and GABA receptors. GABA (gamma-amino-butyric acid) is the predominant inhibitory transmitter in the mammalian CNS. It has been postulated (Olney et al. 1991) that the efficacy of certain barbiturates in preventing the neurotoxic actions of NMDA antagonists stems from their ability to act as direct GABA agonists that can activate GABA type A ($GABA_A$) receptors even in the absence of GABA.

(3) diazepam (marketed under the trade name VALIUM), a drug in the benzodiazepine class, confers partial protection against NMDA antagonist neurotoxicity (Olney et al. 1991). The receptor system with which benzodiazepines interact (called the benzodiazepine receptor) is considered a component part of the GABAA receptor complex. Therefore, it has been postulated that the action of diazepam in protecting against NMDA antagonist neurotoxicity is due to its influence on $GABA_A$ receptor activity. The observation that diazepam provides only partial protection (in contrast to more complete protection by barbiturates) may relate to the fact that diazepam does not, like barbiturates, act as a direct GABA agonist even in the absence of GABA; rather, the action of diazepam is dependent upon GABA being present and is limited to potentiating the action of GABA.

(4) certain drugs that bind to a class of receptors called sigma receptors (Farber et al 1993). These drugs include di(2-tolyl)guanidine and rimcazole, which act selectively at sigma receptors, as well as other drugs such as haloperidol, thioridazine and loxapine, which interact with dopamine receptors as well as sigma receptors.

Non-NMDA Antagonists as Safener Agents for Preventing Adverse Side Effects of NMDA Antagonist Drugs Despite the discoveries of the above safening agents which can be used to reduce the toxic side effects of NMDA antagonists, there remains a need for improved treatments which take advantage of the beneficial effects of NMDA antagonists, while avoiding the adverse side effects NMDA antagonists. In particular, it would be advantageous to find agents that actually improve the efficacy of NMDA antagonists as neuroprotective drugs while simultaneously preventing the neurotoxic side effects of NMDA antagonists. The Applicant has discovered that non-NMDA antagonists are agents that have these properties.

Accordingly, one of the objects of the present invention is to disclose a method of using NMDA antagonist drugs in combination with non-NMDA antagonist drugs to fulfill the dual beneficial purpose of achieving a greater degree of neuroprotection against acute CNS injury syndromes than can be achieved with either class of agent by itself while also reducing or preventing the adverse CNS neurotoxic side effects of the NMDA antagonist.

Another object of this invention is to disclose a method of using a non-NMDA antagonist together with an NMDA antagonist to permit the NMDA antagonist to be used more safely and potentially more effectively for protecting against excitotoxic neurodegeneration in chronic neurodegenerative disorders such as ALS, Alzheimer's disease, AIDS dementia, parkinsonism and Huntington's disease.

Another object of this invention is to disclose a method of using a non-NMDA antagonist together with an NMDA antagonist to permit the NMDA antagonist to be used more safely for controlling neuropathic pain.

Another object of this invention is to disclose a method of using a non-NMDA antagonist together with an NMDA antagonist to permit the NMDA antagonist to be used more safely for preventing the development of tolerance to, dependence on, and craving for opiates or other addictive drugs.

SUMMARY OF THE INVENTION

The present invention relates to the use of drugs which act as kainic acid receptor antagonists (KA antagonists) as "safener" agents for reducing or preventing the toxic side effects caused by other drugs known as NMDA antagonists. It is well-established that NMDA antagonist drugs can reduce excitotoxic brain damage during or following ischemic or hypoxic events such as stroke, cardiac arrest, or asphyxia. This invention discloses that simultaneous suppression of activity at kainic acid receptors can enhance and improve the therapeutic benefits of NMDA antagonists, through two distinct mechanisms: (1) KA antagonists can provide a safening effect, to reduce or prevent the toxic side effects caused by NMDA antagonists, and (2) KA antagonists, when co-administered with NMDA antagonists, can increase the extent of neuronal protection provided to the CNS, beyond the levels of protection that can be provided by NMDA antagonists alone, or non-NMDA antagonists alone. This method allows NMDA antagonists to be used safely and effectively for purposes such as (1) reducing excitotoxic brain damage and controlling intracranial pressures following an acute CNS insult such as stroke, cardiac arrest, or CNS trauma; (2) reducing excitotoxic brain damage caused by a chronic neurodegenerative disease; (3) alleviating neuropathic pain; (4) preventing or reducing tolerance or addiction to potentially addictive drugs; and (5) human and veterinary anesthesia.

DESCRIPTION OF THE PREFERRED EMBODIMENTS

Figure 1:
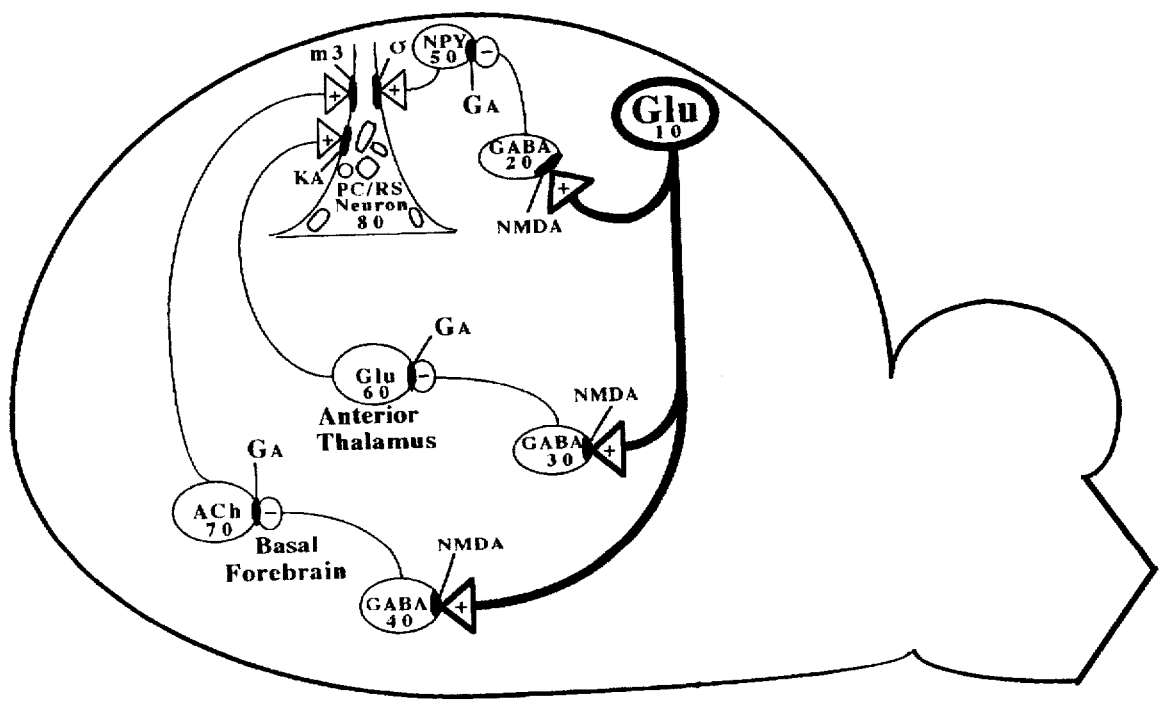
FIG. 1 is a schematic depiction of a neural circuit in the brain. In this circuit, the release of glutamate by neuron 10 stimulates GABAergic neurons 20, 30, and 40, causing them to release GABA, an inhibitory neurotransmitter. The secreted GABA acts to suppress excitation of other neurons 50, 60, and 70, in a manner that protects a pyramidal neuron 80 against lethal overstimulation. A kainic acid (KA) receptor is shown on the surface of the pyramidal neuron; if this receptor is blocked by a KA receptor antagonist, then such KA-blocking activity will help protect the pyramidal neuron against vacuole formation and mitochondrial dissolution that would otherwise be caused by an NMDA antagonist.

This invention relates to the use of drugs (referred to herein as KA antagonists) which can penetrate the mammalian blood-brain barrier and suppress glutamate- or aspartate-mediated excitatory activity at the subclass of neuronal glutamate receptors known as kainic acid (KA) receptors. Such KA antagonists, when co-administered with NMDA antagonists that suppress excitatory activity at the subclass of glutamate receptors known as NMDA receptors, can act as "safener" agents to reduce or prevent the toxic side effects caused by the NMDA antagonists.

It has been known for years that NMDA antagonists have the potential to reduce excitotoxic brain damage during or following ischemic or hypoxic events such as stroke, cardiac arrest, or asphyxia; more recently, it has also been discovered that NMDA antagonists also have certain other beneficial potentials, in alleviating neuropathic pain and in preventing or reducing tolerance or addiction to potentially addictive drugs. However, no NMDA antagonists have been approved for use in humans (excluding certain very limited experimental use) because NMDA antagonists are known to cause several adverse side effects, including (1) pathomorphological changes to neurons (including neuronal death) in certain regions of the brain, and (2) psychotomimetic effects, such as hallucinations.

It is also been known that NMDA antagonist drugs can cause adverse neurotoxic or psychotomimetic side effects, including (a) formation of vacuoles in neurons in cerebrocortical or limbic brain regions; (b) expression of heat shock proteins in cerebrocortical or limbic brain regions; (c) alteration or loss of mitochondria in neurons; (d) neuronal death; and (e) hallucinations and other psychotomimetic effects.

Accordingly, this invention discloses that when NMDA antagonists are used for therapeutic purposes, simultaneous use of a KA antagonist drug to suppress excitatory activity at KA receptors in the CNS can provide a safening effect which reduces or prevents the toxic side effects caused by the NMDA antagonist.

Furthermore, as disclosed in the above-cited copending parent application, U.S. patent application Ser. No. 07/877,839 (the teachings of which are hereby incorporated by reference), the simultaneous suppression of excitatory activity at both NMDA receptors and KA receptors, using both an NMDA antagonist and a KA antagonist, can increase the level of protection provided to the CNS, beyond the level of protection that can be provided by NMDA antagonists alone or non-NMDA antagonists alone.

Thus, the Applicant has disclosed that the simultaneous or overlapping use of both an NMDA antagonist and a KA antagonist increases both the safety, and the efficacy, of NMDA antagonist drugs, allowing their safe and effective use for purposes which include: (1) reducing excitotoxic brain damage and controlling intracranial pressures, following an acute CNS insult such as stroke, cardiac arrest, asphyxiation, or CNS trauma; (2) reducing excitotoxic brain damage caused by a chronic neurodegenerative disease; (3) alleviating neuropathic pain; (4) preventing or reducing tolerance or addiction to potentially addictive drugs; and (5) human and veterinary anesthesia, while avoiding the unwanted neurotoxic and psychotomimetic side effects listed above.

As described and listed in the Background section, numerous NMDA antagonists are known which can penetrate the mammalian blood-brain barrier, and which may be used as described herein. Pharmaceutical companies have developed an array of NMDA receptors which are effective, and which can be used safely, provided that their toxic side effects can be eliminated or reduced to tolerable levels, by co-administering them with safener drugs as described herein.

KA antagonists which can penetrate the mammalian blood-brain barrier, and which are good candidates for use as described herein, include, for example, the quinoxalinedione derivatives described in the PCT applications assigned to Schering AG and Novo Nordisk, including applications Wo-94/25469, WO-94/25470, WO-94/25472, WO-93/06103, and WO-94/21639. These quinoxalinedione derivatives are regarded as "third generation" quinoxalinediones, since they were created after NBQX, a second-generation quinoxalinedione which improved over the first generation of quinoxalinediones (CNQX and DNQX). As such, the third generation quinoxalinediones described in the above-cited PCT applications are believed to overcome certain limitations of NBQX which related to low solubility in aqueous solutions.

As noted above, all currently known KA antagonists also have substantial affinity for QUIS/AMPA receptors; accordingly, such drugs are often referred to as non-NMDA antagonists, rather than specifically as KA or QUIS/AMPA antagonists. To the best of his knowledge, the Applicant is the first researcher to discover the functionally important distinction that KA receptors but apparently not QUIS/AMPA receptors are located on the surfaces of the PC/RS pyramidal neurons which are damaged by the toxic side effects of NMDA antagonists.

As noted above, a number of drugs have been discovered which tend to suppress activity both at NMDA receptors, and non-NMDA receptors. However, two important advantages can be provided by administering two distinct and independent drugs to a patient in need thereof, where one drug is an NMDA antagonist and the other drug is a non-NMDA antagonist.

First, the use of two drugs, in combination, allows a doctor to carefully control the ratio and the optimal dosage of the two drugs, regardless of their potency. Instead of trying to balance two different (and in certain respects competing) activities of a single drug, it is far easier to have two distinct degrees of control, by administering each drug and controlling each level of activity separately.

In addition, the use of two different drugs allows a doctor to administer the drugs in a time-dependent sequence, if desired. In particular, the results that have been observed in in vivo animal tests when NMDA and non-NMDA antagonists were compared to each other have indicated that the NMDA antagonist may be of greatest benefit if administered as quickly as possible after the onset of a stroke or other ischemic event, while the desired benefit from the non-NMDA antagonist may be obtained even if it is not administered until an hour or more later. While it might be considered advantageous under many circumstances to administer both drugs as early as possible, the simultaneous administration of both drugs in substantial dosage may cause dangerous and potentially lethal side effects, such as depression or cessation of cardiorespiratory function. In order for a non-NMDA antagonist to provide optimal protection against the toxic side effects of an NMDA antagonist, it may be preferable for the non-NMDA antagonist to be administered in an overlapping manner with the NMDA antagonist, but not in a manner that causes peak concentrations in the blood and brain to occur simultaneously. Therefore, having the flexibility to administer the drugs in a planned sequence, or in a sequence that can be varied depending on the changing status of the patient, is preferable.

The use of two drugs provides these advantages, while the use of a single broad-spectrum Glu antagonist does not.

Neuronal Circuitry and Disinhibition

For a number of years, the Applicant (who has been involved in the discovery of numerous different mechanisms involved in excitotoxicity) has been testing various types of neuroactive drugs, to help elucidate the role of different neuronal receptors systems in excitotoxicity and in the toxic side effects caused by NMDA antagonists. The neural circuit diagram in FIG. 1 is based on data gathered in recent experiments by the Applicant, and it has not been published prior to the filing of this application.

Referring to FIG. 1, glutamate is released, in tiny amounts but on a continuous or nearly-continuous basis, by synapses that emerge from a neuron labelled as GLU neuron 10. Glutamate molecules being released by neuron 10 react with and activate NMDA receptors on the surfaces of three neurons 20, 30, and 40, which are called "GABAergic" neurons since they release GABA (gamma-amino butyric acid, an inhibitory neurotransmitter). This slow and steady release of glutamate by neuron 10 provides a steady, continuous driving force that keeps GABAergic neurons 20, 30, and 40 in a constant state of activity, resulting in frequent or continuous release of GABA onto GABA receptors on three different types of excitatory neurons 50, 60, and 70. These excitatory neurons release Neuropeptide Y (NPY) from neuron 50, glutamate (Glu) from neuron 60, or acetylcholine (ACh) from neuron 70.

Thus, glutamate, via its driving action on GABAergic inhibitory neurons, exerts "tonic inhibition" on neurons 50, 60, and 70. The word "tonic" implies that this mechanism maintains a relatively constant level of inhibitory tone, which restrains the activity of three excitatory pathways which use NPY, glutamate, or ACh as excitatory neurotransmitters.

This represents an important principle (and an apparent paradox) of CNS activity. An excitatory neurotransmitter such as glutamate can cause suppression, rather than excitation, of neuronal activity. This is important, not only for physiological functions in the CNS, but for understanding how "disinhibition" can contribute to neuronal damage and death when NMDA antagonists are used. If the NMDA receptors that govern GABAergic neurons 20, 30, and 40 in FIG. 1 are blocked by an NMDA antagonist, then the ability of neuron 10 to tonically inhibit the three excitatory neurons 50, 60, and 70 (via GABAergic neurons 20, 30, and 40) is lost. This loss of glutamate-mediated control is referred to herein as "disinhibition" of the inhibitory control mechanism that normally protects pyramidal neuron 80. When disinhibition is caused by NMDA antagonist drugs, all three excitatory neurons 50, 60, and 70 can begin to release undesirably high levels of their excitatory neurotransmitters.

All three of the excitatory neurons 50, 60, and 70 are coupled via axons to pyramidal neuron 80, located in the posterior cingulate or retrosplenial (PC/RS) cortex of the brain. If all three excitatory neurons 50, 60, and 70 begin firing simultaneously, they can overstimulate pyramidal neuron 80 and begin pushing it to the point where it becomes so exhausted that it can suffer serious damage and eventually die from overstimulation.

The highly simplified schematic depiction in FIG. 1 indicates that a single glutamate-releasing neuron 10 interacts with all three GABAergic inhibitory neurons 20, 30, and 40, and that each GABAergic inhibitory neuron governs a single excitatory neuron 50, 60, or 70. This simplified arrangement is shown in the figure, merely to avoid excessive clutter in the drawing; in the extraordinarily complex circuitry of the brain of a higher animal, a single neuron can have hundreds or even thousands of signal-transmitting or signal-receiving synaptic junctions with other neurons, and thousands and possibly millions of glutamate-releasing neurons will interact to sustain tonic inhibition of neuronal circuits involving thousands and possibly millions of inhibitory neurons. The important point is that many and perhaps most of these neuronal interfaces are mediated by glutamate release and NMDA receptors in the manner shown in the drawing, and the tonic inhibition circuitry can be suppressed and rendered incompetent by NMDA antagonist drugs.

Similarly, pyramidal neuron 80 represents merely one of thousands or millions of neurons which are placed at risk when NMDA antagonist drugs are administered, and the neurons which are jeopardized are scattered widely throughout a number of different corticolimbic regions of the brain. The PC/RS cortical region is the focal point of the histological examinations described in the Examples, not because it is the only site of damage, but because it is one of the most heavily and consistently damaged areas in the brain; since it is a highly sensitive and vulnerable region of the brain where damage will reliably appear when damage is being caused as a toxic side effect by an NMDA antagonist drug, this region is used as an indicator region for purposes of examination.

The pyramidal neuron 80 is shown as having three different types of excitatory receptors: (1) kainic acid (KA) receptors, a type of non-NMDA glutamate receptor; (2) m3 receptors, a type of muscarinic acetylcholine (ACh) receptor; and, (3) sigma receptors, which are believed to be triggered by neuropeptide Y (NPY). The presence of all three types of excitatory receptors on pyramidal neurons is supported by the experimental evidence gathered by the Applicant.

After discovering that blockade of NMDA receptors can disrupt the brain's inhibitory control of all three excitatory pathways (KA receptors, sigma receptors, and muscarinic receptors) that innervate PC/RS cerebrocortical neurons, the Applicant undertook a series of experiments to evaluate the relative importance of each of the three pathways. In these experiments, combinations of specific receptor agonists were microinjected into the cingulate cortex; this type of direct injection into certain targeted regions of the brain minimized any experimental uncertainties over whether the observed effects may have been due to actions in other regions of the brain. The three test drugs were kainic acid, an agonist which stimulates KA-type glutamate receptors; SKF-10,047, an agonist that stimulates sigma receptors; carbachol, an agonist that stimulates muscarinic ACh receptors. In some test animals, only one of these drugs was injected. In other animals, various combinations of two drugs were injected (mixed together in a "cocktail"). In still other animals, all three drugs were injected, mixed together.

In animals injected with all three drugs, a neurotoxic reaction was found in cingulate cortical neurons, which was identical to the toxic reaction that is caused by subcutaneous administration of MK-801, an NMDA antagonist. However, in animals injected with any two (or only one) of the three drugs, no such toxic reaction was found.

These results, which corroborate the circuit diagram depicted in FIG. 1, indicate that the toxic side effects of NMDA antagonist drugs requires simultaneous hyperactivation of all three of these types of receptors (i.e., KA receptors, sigma receptors, and muscarinic receptors) on the surfaces of pyramidal neurons or other neurons in cortical or limbic regions of the brain.

A major implication of these results is that, in order to reduce or prevent the toxic side effects caused by NMDA antagonists, blockade of any one of these three receptor systems (i.e., kainic acid, sigma, or muscarinic receptors) can be sufficient. That discovery provided the foundation of this invention, which discloses that the toxic side effects caused by NMDA antagonists can be reduced or eliminated by suppressing activity at KA receptors.

SUMMARY OF EXAMPLES

This section provides an overview of the Examples, to place them in context and describe their significance.

The first five examples have been essentially repeated from copending parent application Ser. No. 07/877,839, which can be consulted for further details if desired. These five examples provide data showing that a combination of an NMDA antagonist and a non-NMDA antagonist (i.e., a KA antagonist) provide a higher level of protection against excitotoxic neuron damage than either drug can provide when acting alone, even in unlimited quantities.

The first example describes an in vitro assay using pieces of retinal tissue from embryonic chickens. As noted therein, the experimental findings that CNQX could substantially boost the neuroprotective effects of an NMDA antagonist were received with skepticism by other scientists working in this field, because that result was at odds with evidence being reported by several other laboratories using other ischemia assays. Other laboratories were claiming that NMDA antagonists, by themselves, provided excellent protection against ischemic neurodegeneration, and that non-NMDA antagonists alone did not provide protection and did not increase the level of protection provided by NMDA antagonists.

Since the disputed results pertained to in vitro preparations of non-adult neurons from a non-mammalian species, the Applicant undertook the development of a more relevant assay system for studying CNS ischemic neuronal degeneration, using in vivo tests that involved intact, adult mammals, and which generated actual ischemia rather than merely chemically-simulated ischemia. That assay is described in Example 2, and is described in more detail in Mosinger and Olney 1989.

The in vivo assay in Example 2 uses a dye (rose bengal) which triggers a blood-clotting mechanism if a bright light is shone upon it. This dye was injected into the tail veins of anesthetized rats, and a bright light was shone into the eyes of the rats, triggering blood clot formation and severe ischemia in the retinal tissue of the animals. The rats were divided into different treatment groups, and in each animal, one eye was treated as a control (injected with saline solution), while the other eye had been injected with an NMDA antagonist only, a KA antagonist only, or a combination of an NMDA antagonist plus a KA antagonist. The rats were sacrificed after an hour, and retinal neurons from both eyes were examined microscopically to quantify the extent of neuronal damage. These tests showed clearly that in adult mammalian animals, a combination of an NMDA antagonist and a KA antagonist provided a substantially higher level of protection than either drug could provide when acting alone.

Example 3 describes the same experiment, repeated with a different KA antagonist drug. The tests in Example 2 used a KA antagonist called CNQX, which cannot penetrate a mammalian BBB and enter the CNS in substantial quantities. After those tests had been completed, an improved KA antagonist called NBQX, which can penetrate the BBB, was announced and provided to the Applicant by Novo Nordisk, the Danish company which created it. Accordingly, the Applicant repeated the experiments using the new drug, NBQX. The results were the same as with CNQX: a combination of NBQX with an NMDA antagonist provided a substantially higher level of protection than either drug could provide by itself.

Example 4 describes the same in vivo experiment, repeated with yet another KA antagonist called GYKI 52466. Again, the results were the same: a combination of GYKI with an NMDA antagonist provided a substantially higher level of protection than either drug could provide by itself.

And in Example 5, a similar experiment was repeated with two broad-spectrum glutamate antagonists, kynurenate and 7-chlorokynurenate. Each of these drugs is a single drug that can block both NMDA and KA receptors, comparable to a mixture of an NMDA antagonist with a KA antagonist. Either of these drugs could provide a substantially higher level of protection than any selective NMDA antagonist or KA antagonist could provide by itself. These drugs are not useful, however, as therapeutic agents for preventing CNS damage due to stroke or other forms of ischemia, since neither can penetrate the blood-brain barrier.

As noted above, Examples 1–5 repeat the results of several experiments that were done several years ago and disclosed in U.S. application Ser. No. 07/877,839, which was filed in 1992. By contrast, Examples 6–8 disclose the results of a different and more recent series of experiments, which have not been previously disclosed or published.

In the tests described in Example 6, the Applicant showed that three different excitatory pathways (involving sigma receptors, KA-type glutamate receptors, and muscarinic-type acetylcholine receptors, as depicted in FIG. 1), are all involved in mediating the toxic damage to pyramidal neurons in the posterior cingulate and retrosplenial (PC/RS) regions of the brain, which is caused by NMDA antagonists. This was shown by microinjecting combinations of several receptor agonists directly into the cingulate cortex of the brains of adult rats; this type of direct injection into the brain was done to avoid problems of limited permeability through blood-brain barriers. The test drugs included an agonist that stimulates sigma receptors, an agonist that stimulates muscarinic receptors, and kainic acid, which stimulates KA receptors.

In some test animals, only one of these drugs was injected. In other animals, various combinations of two drugs were mixed together and injected. In still other animals, all three were mixed together and injected.

In animals injected with all three drugs, a neurotoxic reaction was found in cingulate cortical neurons, which was identical to the toxic reaction that is caused by subcutaneous administration of MK-801, an NMDA antagonist. However, in animals injected with only two (or only one) of the three drugs, no such toxic reaction was found. These results indicate that NMDA antagonist neurotoxicity involves excessive activation of all three of these receptor systems, and that blockade of any one of these systems can prevent or substantially reduce such neuronal damage.

In Example 7, NBQX was microinjected directly into the PC/RS cortex of rats, at several doses ranging from 5 to 50 nmols. The rats were also injected subcutaneously with a dosage of a potent NMDA antagonist (MK-801) which reliably causes vacuoles in PC/RS neurons if no safener drug is used. In these tests, the microinjected NBQX reduced the MK-801 side effects in a dose-dependent manner, and doses of 25 nmol or higher totally prevented the PC/RS vacuole reaction.

In Example 8, NBQX was injected systemically into rats, via the intraperitoneal cavity in the abdomen. As in Example 7, the NBQX was able to reduce (or, in many animals, completely prevent) the toxic side effects of MK-801.

Collectively, the results of Examples 6, 7 and 8 show that use of a KA antagonist drug to suppress activity at KA receptors can reduce (and in some cases entirely prevent) the toxic side effects of NMDA antagonists. The data gathered by the Applicant also indicate that if a KA antagonist is injected into the blood in a manner which sustains a substantial quantity in the bloodstream throughout the 4 hour period during which the toxic side effects of NMDA antagonists typically evolve, then those toxic side effects can be completely prevented. If a KA antagonist which has a short half-life in the blood is used (such as NBQX), this can be accomplished by injections at suitable spaced intervals, such as every half-hour or hour, depending on the rate of metabolic elimination of the agent. Alternately, if a different KA antagonist is used which has a longer half-life in the blood, less frequent injections (or a single injection) may be sufficient.

In summary, the results of Examples 6-8, when considered in conjunction with the results of Examples 1-5, show that coadministering a KA antagonist with an NMDA antagonist can provide two distinct and highly beneficial results: (1) it can increase the level of protection against excitotoxic or other damage, beyond any levels that can be provided by either agent alone; and, (2) it can also improve the safety of the treatment regimen, by reducing or eliminating the toxic side effects of NMDA antagonists.

Modes of Administration

The preferred dosage and mode of administration of a KA receptor antagonist for preventing the toxic side effects of NMDA antagonists will depend upon a number of factors. For example, if a KA receptor antagonist is coadministered as a "safening" agent along with an NMDA antagonist that is being used to prevent excitotoxic brain damage, then the relevant factors will include (1) the potency and dosage of the NMDA antagonist being used; (2) the abilities of the NMDA antagonist and the KA receptor antagonist to penetrate the blood-brain barrier; (3) the severity of the neurotoxic side effects produced by that NMDA antagonist in the absence of a safening agent; and, (4) whether the KA receptor antagonist is being administered before, after, or simultaneously with the NMDA antagonist.

The quantity of a KA receptor antagonist which should be co-administered with an NMDA antagonist is that dosage required to prevent or minimize the appearance of neurotoxic manifestations when that NMDA antagonist is used. Such neurotoxic manifestations, and the dosage of a candidate KA receptor antagonist which can avoid such toxic manifestations, can be determined by tests on rodents or primates which search for cellular manifestations in the brain, such as vacuole formation, mitochondrial damage, heat shock protein expression, or other pathomorphological changes in neurons of the cingulate and retrosplenial cerebral cortices.

These cellular changes can also be correlated with abnormal behavior in lab animals. In human patients, since direct examination of brain tissue is not feasible, the appearance of hallucinations or other psychotomimetic symptoms, such as severe disorientation or incoherence, should be regarded as signals indicating that potentially neurotoxic damage is being generated in the CNS by an NMDA antagonist. Additionally, various types of imaging techniques, such as CAT scans, MRI imaging, and techniques that used labelled substrates to identify areas of maximal activity in the brain, may also be useful for determining preferred dosages of KA receptor antagonists for use as described herein, with or without NMDA antagonists.

The terms, "drug" and "antagonist," as used herein, include so-called "pro-drugs" which are administered in a form that is known and intended to be metabolized, inside a patient's body, into a different form which has a specific desired activity.

The compositions of this invention may be administered by any suitable route which will introduce the intended drug(s) into the bloodstream. Depending on the specific NMDA antagonist and/or KA receptor antagonist being used, the main candidate routes of administration will generally include oral ingestion of tablets, capsules, or liquids; intramuscular, or intravenous injection; subcutaneous implantation of slowrelease devices or formulations or osmotic mini-pumps; transmembrane routes, such as lozenges, sublingual tablets or wafers, chewing gum, intranasal sprays, skin patches, or permeating lotions or ointments; and rectal suppositories, such as for non-physician administration to patients who cannot be relied upon to take their medicine.

Alternately, if a KA antagonist and/or NMDA antagonist cannot penetrate the BBB in the desired quantities, or if they cannot reach an ischemic area of the brain with sufficient speed due to blockage of an artery by a blood clot, dislodged bacterial vegetation or fatty deposit, or any other occlusion, then either or both of such drugs can be introduced into the brain in a manner that bypasses the blood-brain barrier, by direct injection through a small hole drilled through the skull, into a cerebral ventricle (i.e, into one of the sinuses in the brain in which cerebrospinal fluid gathers during its passage through the brain and down into the spinal cord). Although direct injection of a drug into a brain ventricle through the skull is a substantially more complex procedure than simple intravenous injection, the drugs described herein can offer a high level of protection against the type of permanent brain damage caused by massive strokes, total cardiac arrest, and other conditions that will kill or permanently cripple patients if direct and effective intervention is not provided.

The novel preparations of this invention comprise a KA antagonist mixed together with an NMDA antagonist. This mixture can be diluted by a pharmaceutically acceptable carrier, or enclosed within a carrier device such as a capsule. When the carrier serves as a diluent, it may be a solid, semisolid or liquid material which acts as a vehicle, excipient or medium for the active ingredient. Thus the composition can be in the form of tablets, pills, powders, lozenges, chewing gum, cachets, elixirs, emulsions, solutions, syrups, suspensions, aerosols (as a solid or in a liquid medium), ointments containing for example up to ten percent by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propyl- hydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

For oral administration, the compositions of this invention can be admixed with carriers and diluents molded or pressed into tablets or enclosed in gelatin capsules. Alternatively, the mixtures can be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated or packaged in a unit dosage form, each dosage unit containing an effective amount of a KA receptor antagonist. The term "unit dosage form" refers to physically discrete units (such as capsules, tablets, or loaded syringe cylinders) suitable as unitary dosages for human subjects and other mammals, each unit containing a predetermined quantity of active material or materials calculated to produce the desired therapeutic effect, in association with the required pharmaceutical carrier.

The amount of KA receptor antagonist preferred for a unit dosage will depend upon the solubility, potency, and BBB-permeability of the KA antagonist, and upon the solubility, potency, and BBB-permeability of the NMDA antagonist which is being coadministered with the KA antagonist. Except when responding to acute events (such as stroke, cardiac arrest, or asphyxiation, when higher dosages may be required), the preferred dosage of a KA receptor antagonist will usually lie within the range of about 0.001 to about 1000 mg, and more usually from about 0.01 to about 500 mg per day. The amount of the NMDA antagonist will also depend upon the solubility, potency, and BBB-permeability of the NMDA antagonist, and will typically be within the range of from about 0.001 to about 1000 mg, more usually from about 0.01 to about 500 mg per day.

In addition, preferred KA and NMDA dosages will depend not just upon the drugs used, but also upon the medical status and other traits of the patient being treated. For example, if a patient suffering a major stroke is being maintained on a mechanical respirator, so that respiratory depression is not a risk, KA and NMDA antagonists can be administered in dosages that would provide a potentially lethal risk of respiratory depression in patients who are not maintained on mechanical respirators. Accordingly, it will be understood that the amount of selected KA and NMDA antagonists administered for the purposes described herein will be determined by a physician in light of all relevant circumstances, including the condition or conditions to be treated, the choice of composition to be administered including the particular KA and NMDA antagonist(s), the age, weight, and response of the individual patient, the severity of the patient's symptoms, and the chosen route of administration. Therefore, the above dosage ranges are intended to provide general guidance and support for the teachings herein, but are not intended to limit the scope of the invention.

EXAMPLES

As noted above, Examples 1–5 are from copending parent application Ser. No. 07/877,839, and show that an increased level of neuronal protection can be provided by a combination of a KA antagonist and an NMDA antagonists, compared to either agent acting alone. Examples 6–8 describe the ability of KA antagonists to reduce or prevent the toxic side effects of NMDA antagonists.

EXAMPLE 1
In Vitro Embryonic Chick Retina Assay

The Applicant has used a chick embryo retina assay for screening drugs to evaluate their ability to protect against excitotoxic neuronal degeneration, such as occurs under hypoxic/ischemic conditions. In the chick retina assay, ischemia (lack of blood supply) is simulated by eliminating the two major constituents of blood (glucose and oxygen) that CNS tissues depend upon for energy. After 30 min of incubation under oxygen/glucose deprivation, chick retina tissue displays a neurodegenerative reaction similar to that observed when the retina is incubated in medium containing a toxic concentration of glutamate.

Using that assay, the Applicant and his coworkers conducted a pilot study and reported in a brief abstract (Price et al 1988) that the NMDA antagonist MK-801 or the non-NMDA antagonist CNQX provided little or no protection against simulated ischemia when either agent was used by itself, but that a mixture of MK-801 (500 nanomolar, nM) and CNQX (100 micromolar, µM) could prevent ischemic damage simulated as described above in isolated chick retina tissue.

The above findings were received with skepticism by other scientists working in this field, because the results were at odds with evidence being reported at roughly the same time by several other laboratories using other in vitro simulated ischemia preparations. Other laboratories were claiming that NMDA antagonists, by themselves, provided excellent protection against ischemic neurodegeneration, and that non-NMDA antagonists alone did not provide protection and did not increase the level of protection provided by NMDA antagonists.

One contradictory report that deserves particular note was Zeevalk and Nicklas 1991, which reported diametrically opposite results using the same type of chick embryo retina preparations used by the Applicant. Zeevalk and Nicklas 1991 reported that an NMDA antagonist, by itself, protected very effectively while a non-NMDA antagonist conferred no protection at all. However, after the appearance of that directly contradictory result, the Applicant performed a painstakingly careful appraisal of his procedures compared to the procedures of Zeevalk and Nicklas, and subsequently discovered, to his surprise, that an apparently innocuous buffer ingredient called MOPS (an acronym for 3-(N-morpholino)-propanesulfonic acid) had a low-to-moderate level of non-NMDA antagonist activity.

This result, when discovered, supported the Applicant's claims and showed that Zeevalk and Nicklas had unknowingly been using a combination of a NMDA antagonist and a non-NMDA antagonist. This series of events is described in more detail in Example 6 in copending parent application Ser. No. 07/877,839.

All of the evidence being disputed between the Applicant and other skilled researchers pertained to in vitro preparations of immature neurons; in addition, the Applicant's assays involved neurons from a non-mammalian species. Accordingly, the Applicant was concerned that such evidence might not be directly applicable to understanding various mechanisms involved in human neurological disorders such as stroke. Therefore, the Applicant undertook the development of a more relevant assay system for studying CNS ischemic neuronal degeneration, using completely in vivo tests that involved intact adult mammals and actual ischemia (i.e., a blockage of blood supply inside the CNS of a living mammal, rather than chemical manipulations in a tissue culture dish). This assay system is described in Example 2, below.

EXAMPLE 2
Photothrombotic Ischemia in Intact Adult Rats

To overcome various limitations and uncertainties in the chick retina in vitro assays, described above, a photothrombosis assay was developed for studying ischemic neuronal degeneration in vivo in intact adult mammals. This assay uses a photosensitive dye called rose bengal, which releases singlet oxygen (a highly reactive atom with an unpaired electron) when bright light having a wavelength of 560 nm is shone upon it. If the dye is in the blood stream, the release of singlet oxygen triggers a blood clotting mechanism that causes a clot to form rapidly in the illuminated blood vessel. This method is described in detail in Mosinger and Olney 1989a.

Briefly, adult rats (female Sprague Dawley rats, 200–300 g) were anesthetized with halothane and placed in a stereotaxic holder. Their pupils were dilated with an eye-drop mixture of phenylephrine hydrochloride and tropicamide. A Hamilton microsyringe guided by a micromanipulator was used to inject 7 µl of saline into the vitreous of the right (control) eye, and 7 µl of solution containing CNQX, a non-NMDA antagonist (60 nmol) and/or MK-801, an NMDA antagonist (30 or 160 nmols) into the left (experimental) eye. Plastic contact lenses with a drop of Goniosol were then placed on the corneas of both eyes.

After fifteen minutes, rose bengal dye (40 mg/kg) was injected intravenously, via the tail vein. It circulated through the heart and throughout the arterial circulation, including the retina. Both eyes were immediately exposed to 7 min of intense light from slide lantern projectors fitted with a 550 nm filter. The light caused the rose bengal dye in the illuminated blood vessels of the retina to release singlet oxygen, which triggered thrombosis (the formation of blood clots) within the retinal tissue. Within a few minutes, the arterial circulation to the retina was totally occluded (blocked by blood clots), leading to ischemia in the retinas of both eyes of each animal.

The rats were killed 1 hr later with an overdose of chloral hydrate. The eyes were removed, and the retinal portions were immersed in glutaraldehyde/paraformaldehyde fixative and processed for examination using a light microscope, as described below.

The experimental design (injecting saline into one eye to serve as a control, while injecting CNQX and/or MK-801 into the other eye) allowed one eye of each animal to serve as an internal control for each experiment. If the photothrombosis reaction did not work because the dye was not successfully administered, it would be detected as a photothrombosis failure (no histological damage) in the control eye, and that particular animal could be removed from the groups being analyzed. In practice, photothrombosis failure rarely occurred; one hour after the occlusion, the control eyes of the test animals quite consistently showed signs of a severe cytopathological reaction which closely resembled the excitotoxic type of reaction that occurs in the retina if a toxic dose of glutamate is injected into the vitreous. This type of reaction, whether caused by photothrombosis or by injection of glutamate into the vitreous, consists of severe swelling of neuronal dendrites and cell bodies, with the nuclei of the affected neurons becoming shrunken and dark. These changes occur in three types of retinal neurons referred to as ganglion cell neurons, amacrine neurons, and bipolar neurons. When these neurons show such changes (especially swelling of the cell body and darkening of the nucleus), it is generally considered a sign of irreversible degeneration leading inexorably to cell death. In the very early stages of such a reaction, the first pathological change that can be detected is mild swelling of dendrites. If the reaction is arrested at this stage, the changes are likely to be reversible and the neuron may be saved from cell death if blood circulation is restored before further damage occurs.

CNQX is only sparingly soluble in aqueous medium, and the volume of solution that could be injected into the vitreous of the eye without creating abnormal pressure conditions was limited to approximately 7 µl. Therefore, the highest dose of CNQX that could be administered was 60 nanomoles (nmol, which is $10^{-9}$ moles, only 1/1000th of a micromole). While this dose of CNQX by itself appears to have conferred some protection, the difference in scores between the control and experimental eyes for this group was not statistically significant. Moreover, the range of variation among the experimental eyes treated with CNQX but not MK-801 was considerable, suggesting that any protective effect that may have occurred was highly inconsistent.

MK-801 is quite soluble in aqueous medium (including the vitreous fluid in the eye), and it is such a potent NMDA antagonist that it does not require high doses to block NMDA receptors. In fact, analysis of the data in Table 1 suggests that both of the doses tested (30 and 160 nmol) were high enough to completely block all NMDA receptors. This conclusion follows from the fact that both of the doses tested conferred a similar degree of protection, as would be expected if both blocked the same number of NMDA receptors. The fact that the lower dose provided the same modest degree of protection as the higher dose indicated that a "ceiling effect" had been reached, constituting the maximum amount of protection that can be obtained by using an NMDA antagonist alone.

To evaluate the neuroprotective effects achieved by the two different drugs, light microscopic sections 1 micrometer thick displaying the full extent of each retina were analyzed by two experienced histopathologists. The retinal sections were coded by numbers, so the pathologists were not aware of the treatment conditions. The severity of cytopathology was ranked on a scale of zero to +4, based on the degree of dendritic swelling in the inner plexiform layer and the degree of cytoplasmic swelling and nuclear changes in the neurons of the inner nuclear and ganglion cell layers (the specific neural elements of the retina that selectively undergo degeneration under ischemic conditions or after exposure to a toxic concentration of glutamate). The criteria for scoring were as follows:

0=total absence of cytopathology.

+1=very slight cytopathology, limited to mild swelling of inner plexiform dendritic processes.

+2=more advanced neuronal degeneration with more conspicuous inner plexiform dendritic swelling plus mild to moderate cytoplasmic and nuclear changes in neurons of the inner nuclear and ganglion cell layers.

+3=the same changes as in a +2 lesion but with 50 to 75% of the affected neurons showing more severe changes, signifying an advanced stage of neuronal degeneration.

+4=the same changes as in a +3 lesion but with 75–100% of the affected neurons showing very severe changes, signifying uniformly severe cytopathological involvement across the entire retina.

The scores assigned by the two histopathologists for a given retina were usually in perfect agreement. A few cases varied by a single rating unit; in such cases, an average of the two readings was used to determine the final score.

The results of the various treatments are in Table 1. Differences between the control and experimental eyes were statistically analyzed by the Student's T test. The results indicate that either MK-801 or CNQX by itself provided an equivocal and highly variable amount of protection which could be described as partial at best. The two agents together provided a substantially higher level of protection, with the majority of the retinas being in the 0 or +1 categories.

EXAMPLE 3
In Vivo Assays of MK-801 Combined with NBQX

An important limitation of the above experiments involving a combination of MK-801 and CNQX is that CNQX does not penetrate blood brain barriers and, therefore, could not provide a means of treating neuronal degeneration occurring in the brain under ischemic conditions (unless, perhaps, injected directly into a cerebral ventricle or other brain region, through a hole drilled in the skull).

In 1989 and 1990, Sheardown et al described NBQX (a compound that blocks non-NMDA receptors with higher affinity than NMDA receptors) and showed that NBQX could prevent or reduce neuronal degeneration induced by ischemia in the adult in vivo rat brain. Therefore, the Applicant conducted a new series of studies, similar to the dye-photothrombosis studies described in Example 2, but using NBQX instead of CNQX. The NBQX was a gift from Dr. Tage Honore of Novo Nordisk, in Denmark.

These tests were performed using the same procedures and evaluation criteria described in Example 2. In each animal, one eye (which was injected with saline) served as the control, while the other eye (injected with MK-801 and/or NBQX) was the experimental eye. All injections were of 7 microliters and were made into the vitreous humor of the eye.

In these experiments, MK-801 was tested at 30 nmole per eye. In previous experiments, MK-801 had been tested by itself over a wide range of dosages (ranging from 3 to 160 nmoles) and it was found that MK-801 quickly reaches a "ceiling level" of protection; any dose in excess of 10 nmoles provided approximately 25–40% protection, with considerable variability from one experiment to another, regardless of dose. The 40% protection level was the maximum amount of protection obtainable with MK-801 by itself, and increasing the dose beyond 10 nmoles did not provide any additional protection. Nevertheless, the Applicant tripled the 10 nmole dosage and administered 30 nmoles, in order to give MK-801 every opportunity to provide as much protection as possible.

The NBQX was tested at only one dose (60 nmoles) because it is subject to solubility limitations as described above for CNQX.

The data were gathered using the scale of damage ranging from 0 for no detectable damage to +4 for extreme damage, as described above. Mean values were calculated for all similarly treated eyes, and the mean values for treated and untreated (saline control) eyes were compared.

The results indicated that NBQX, when administered by itself to 8 rats, reduced the level of damage by about 30%, while MK-801, when administered by itself to 16 rats, reduced the level of damage by 40%.

By contrast, when NBQX was administered in combination with MK-801, damage was reduced by 82%.

These results clearly indicate that when an NMDA antagonist which penetrates the blood brain barrier is administered in conjunction with a non-NMDA antagonist which also penetrates the blood-brain barrier, the combination reduces neurotoxic ischemic damage in CNS neurons by a much greater degree than either drug acting alone can provide, even in unlimited quantities. The NMDA antagonist MK-801 was tested across a wide dosage range and was shown to be subject to a ceiling effect when used by itself; a maximal amount of protection (40% or less) was all that could be obtained, regardless of quantity. Similarly, in a separate set of tests, NBQX was used at a dose which was as high as solubility limitations permitted, yet it was not able, by itself, to provide more than about 30% protection against ischemic damage. Despite those ceiling limitations on both of the component drugs, the Applicant demonstrated that 80% protection could be achieved when the two drugs were combined. Thus, combining the two drugs provided a level of protection vastly superior to the protection that either type of agent could accomplish by itself.

EXAMPLE 4
In Vivo Assays of MK-801 Combined with GYKI 52466

In 1990, in a publication that appeared after the filing of parent application Ser. No. 07/467,139, Tarnawa et al reported the discovery that a drug designated as GYKI 52466 (referred to herein as GYKI; the full chemical name is 1-(amino-phenyl)-4-methyl-7,8-methylenedioxy-5H-2, 3benzodiazepine) penetrates the BBB and selectively inhibits activity at non-NMDA receptors, primarily QUIS/AMPA receptors. This was shown in tests which involved the inhibition of spinal cord reflexes in cats; these tests did not involve ischemia, and Tarnawa et al did not teach or suggest that GYKI 52466 could be combined with other drugs such as NMDA antagonists for treatment of ischemia.

GYKI has an entirely different structure than quinoxalinediones such as CNQX and NBQX. It belongs in the general category of benzodiazepines, which are primarily of interest as tranquilizers because 1,4-benzodiazepines stimulate activity at inhibitory receptors known as gamma-aminobutyric acid (GABA) receptors. By contrast, GYKI is a 2,3-benzodiazepine which apparently has little or no effect at GABA receptors.

The Applicant tested a sample of GYKI (a gift from Dr. Istvan Tarnawa of the Institute for Drug Research in Budapest, Hungary) in the in vivo photothrombosis assay described in Examples 2 and 3, with and without co-administration of MK801. Because of solubility limitations when aqueous buffer was used, the maximum dosage of GYKI that could be administered without injecting excessive quantities of fluid into the vitreous of the eye was 100 nmoles.

The tests indicated that GYKI 52466, administered by itself to 6 rats, reduced neuronal damage by 25%. As noted above, MK-801, reduced the level of damage by 40% when administered at 30 nmol per eye.

However, when a combination of GYKI and MK-801 was administered, damage was reduced by 71%. This level of protection was much greater than either component could achieve by itself.

In subsequent tests, the Applicant has administered substantially higher quantities of GYKI (up to 500 nm), by dissolving it in dimethyl sulfoxide (DMSO) rather than aqueous solution. When administered at higher quantities, the maximal level of protection afforded by GYKI is in the range of about 40%, using the criteria described above.

When the maximal effective dosage of GYKI is combined with a relatively low quantity of MK-801 which provides only about 15% protection, the combination provides a protection level of about 80%. Again, this is far superior to any protection level that can be provided by either component drug by itself.

EXAMPLE 5
In Vivo Assay using Broad-Spectrum Glutamate Antagonist

It has been shown in several in vitro preparations that kynurenate, or its structural analog, 7-chlorokynurenate, have broad-spectrum blocking action against the neurotoxic action of both NMDA and non-NMDA agonists, with the potency against NMDA agonists being approximately three times greater than against non-NMDA agonists. Based on the results from the experiments described above, in which it was shown that blocking both NMDA and non-NMDA receptors provided better protection against ischemic damage than blocking only one or the other receptor type, the Applicant reasoned that a broad spectrum glutamate antagonist might provide a high degree of protection against ischemic damage.

Using the in vivo photothrombosis model described above, kynurenate or 7-chlorokynurenate were tested for their ability to protect against ischemic neuronal degeneration. Intravitreal injection of kynurenate or 7-Cl-kynurenate provided partial protection at low doses (wherein the activity presumably was limited to blocking NMDA receptors) and greater than 90% protection at higher doses (both NMDA and non-NMDA receptors blocked).

Neither kynurenate nor 7-Cl-kynurenate can penetrate blood brain barriers. Therefore, these agents do not offer a useful therapeutic agent for preventing CNS damage due to stroke or other forms of ischemia, except possibly if injected directly into cerebral ventricles. However, the kynurenate and 7-Cl-kynurenate results in the photothrombosis assay, in which drugs that have been injected directly into the vitreous do not need to penetrate the BBB to reach the retinal neurons, clearly and directly corroborate and support the Applicant's demonstration that in vivo blockade of both NMDA and non-NMDA receptors in an adult mammal provides optimal protection, whereas only partial protection is achieved by blocking only NMDA receptors or only non-NMDA receptors.

A further implication of these findings is that it does not matter whether a broad-spectrum blockade of NMDA and non-NMDA receptors is achieved by a single agent or a combination of agents. In adult mammals, superior protection is achieved regardless of what particular drug or combination of drugs is used (provided that activity at both NMDA and non-NMDA receptors is inhibited), compared to the degree of protection that can be obtained by blocking only one or the other class of receptor.

EXAMPLE 6
Tests Showing Involvement of Sigma, Muscarinic, and Kainic Acid Receptors in NMDA Antagonist Toxic Side Effects As described in the Background section of this application, NMDA antagonists can cause serious neurotoxic side effects, including degenerative changes in neurons in certain cortical and limbic regions of the brain.

A set of tests was carried out by the Applicant to help elucidate the role of various neuronal systems in the toxic side effects caused by NMDA antagonists. In these tests, combinations of several receptor agonists were microinjected into the cingulate cortex, to minimize any experimental uncertainties over whether the observed effects may have been due to actions in other regions of the brain. These test drugs included (+)SKF-10,047, an agonist that stimulates activity at sigma receptors; carbachol, an agonist that stimulates activity at muscarinic-type acetylcholine receptors; and kainic acid, an agonist which stimulates KA-type non-NMDA glutamate receptors. These drugs were selected because in other recent studies the Applicant had generated evidence potentially implicating three types of receptors (muscarinic, sigma and kainic acid) as proximal mediators of the toxic action of NMDA antagonists in the cingulate cortex.

In some test animals, only one of these drugs was injected. In other animals, various combinations of two drugs were injected (mixed together in a "cocktail"). In still other animals, all three drugs were injected, mixed together.

In animals injected with all three drugs, a neurotoxic reaction was found in cingulate cortical neurons, which was identical to the toxic reaction that is caused by subcutaneous administration of MK-801, an NMDA antagonist. However, in animals injected with only two (or only one) of the three drugs, no such toxic reaction was found.

These results indicate that NMDA antagonist neurotoxicity involves excessive activation of all three of these receptor systems (i.e., sigma receptors, muscarinic-type cholinergic receptors, and non-NMDA glutamate receptors). These results helped establish the neuronal circuitry that is described in the Background section and shown in schematic form in FIG. 1.

From the finding that it requires excessive activation of all three systems for pathomorphological brain changes to occur, it follows that blockade of any one of these systems can prevent or substantially reduce such permanent neuronal damage.

EXAMPLE 7
Protection Against MK-801 Side Effects by Injection of a KA Antagonist into the PC/RS Cortex Based on the finding (described in Example 6) that it requires excessive activation of three separate receptor pathways (muscarinic, sigma, and kainic acid) on PC/RS neurons for NMDA antagonist neurotoxicity to occur, the Applicant postulated that blockade of kainic acid receptors might be sufficient to prevent this type of neurotoxic reaction.

To test this hypothesis, the Applicant administered MK-801 subcutaneously to adult female rats in a dose (0.5 mg/kg) that has been shown previously to consistently induce a fully developed neurotoxic reaction consisting of acute vacuole formation in the majority of pyramidal neurons in layers III and IV of the PC/RS cortices. Some rats received only MK-801, while others were treated simultaneously with NBQX, which blocks both kainic acid and Quis/AMPA receptors. The NBQX was administered by microinjection directly into the PC/RS cortex at one of several doses ranging from 5 to 50 nmols.

The rats were sacrificed four hours after treatment, and brain tissue from the PC/RS region was histopathologically evaluated by previously described methods (Olney et al 1991) using double-blinded techniques. The number of vacuolated PC/RS neurons were counted on each side of the brain at a rostrocaudal level immediately posterior to where the corpus callosum ceases decussating across the midline (approximately 5.6 mm caudal to Bregma; see Paxinos & Watson, *The Rat Brain in Stereotaxic Coordinates*, 2nd ed., 1986). In previous tests (Farber et al 1993), the Applicants had found that the toxic reaction approaches maximal severity at this level and does not vary much in severity from one animal to another.

The results showed that all animals (n=6) receiving only MK-801 had a severe vacuole reaction in the PC/RS cortex (212 ±7.9 SEM vacuolated neurons per microscopic section), whereas those receiving both MK-801 plus NBQX showed a reduction in the number of vacuolated neurons; this reduction was dependent on the dose of NBQX. All doses of NBQX reduced the number of vacuolated neurons, and the degree of reduction increased progressively as a function of increasing dose with doses ≧25 nmols totally preventing the vacuole reaction.

These findings corroborate that blockade of only one of the three critical receptor pathways on PC/RS neurons is sufficient to prevent the neurotoxic side effects of an NMDA antagonist, and more specifically, showed that blockade of kainic acid receptors can totally prevent this type of neurotoxic reaction.

EXAMPLE 8
Protection Against MK-801 Side Effects by Systemic Administration of a KA Antagonist These experiments were conducted according to a protocol similar to that in Example 7, except that NBQX was administered intraperitoneally instead of intracranially. Adult female rats were treated with MK-801 (0.5 mg/kg sc) alone, or with MK-801 plus NBQX. Although NBQX penetrates blood brain barriers, its half life in the brain is very brief (approximately 15 min). Therefore, NBQX was administered intraperitoneally at the same time as MK-801 and repeatedly every 30 minutes thereafter for a total of 4 injections. The rats were sacrificed four hours after treatment, and brain tissue from the PC/RS region was histopathologically evaluated as described in Example 7.

The animals (n=6) that received only MK-801 had a severe vacuole reaction in the PC/RS cortex (199.3 ±8.1 SEM vacuolated neurons per microscopic section), whereas animals that received both MK-801 and NBQX had a significantly reduced number of vacuolated neurons (52 ±22.4 SEM vacuolated neurons per microscopic section). There was a wide range of variation among the experimental animals, with some rats having no vacuolated neurons and others having a relatively severe reaction. This extreme variance is interpreted as a reflection of the erratic pharmacokinetics of NBQX. It apparently penetrated and remained in the brain of some animals more effectively than in others. This interpretation is supported by the fact that in Example 7 when NBQX was injected directly into the brain it consistently blocked the vacuole reaction at any doses ≧25 nmols.

Thus, there has been shown and described a new and useful means for using drugs which suppress activity at kainic acid receptor, to reduce or eliminate the toxic side effects of NMDA antagonists. Although this invention has been exemplified for purposes of illustration and description by reference to certain specific embodiments, it will be apparent to those 5 skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Backonja, M., et al, "Response of chronic neuropathic pain syndromes to ketamine: a preliminary study," *Pain* 56: 51–57 (1994)

Ben-Eliyahu, S., et al, "The NMDA receptor antagonist MK-801 prevents long-lasting non-associative morphine tolerance in the rat," *Brain Research* 575: 304–308 (1992)

Boast, C. A., "Neuroprotection after brain ischemia: role of competitive NMDA antagonists," *Neurology and Neurobiology* 46: 691–698 (1988)

Choi, D. W., "Glutamate neurotoxicity and diseases of the nervous system," *Neuron* 1: 623–634 (1988)

Choi, D. W., "Excitotoxic cell death," *J Neurobiol* 23: 1261–1276 (1992)

Corso, T, et al, "Ethanol-induced degeneration of dentate gyrus, entorhinal cortex and other olfactory related areas in rat: effects of co-administration of MK-801, DNQX, or nimodipine," *Soc Neurosci Abst* 18: 540 (1992)

Corso, T. D., et al, "Neuron necrotizing properties of phencyclidine," *Soc Neurosci Abst* 20: 1531 (1994)

Davar, G, et al, "MK-801 blocks the development of thermal hyperalgesia in a rat model of experimental painful neuropathy," *Brain Res* 553: 327–330 (1991)

Ellison, G. and Switzer, R. C., "Dissimilar patterns of degeneration in brain following four different addictive stimulants," *Neuroreport* 5: 17–20 (1993)

Farber, N. B., et al, "Antipsychotic drugs block phencyclidine receptor-mediated neurotoxicity," *Biol Psychiatry* 34: 119–121 (1993)

Ferkany, J. W., et al, "Pharmacological profile of NPC 12626, a novel, competitive NMDA receptor antagonist," *J Pharmacol Exp Ther* 250: 100–109 (1989)

Fix, A. S., et al, "Light and electron microscopic evaluation of neuronal vacuolization and necrosis induced by the non-competitive NMDA antagonist MK-801 in the rat retrosplenial cortex," *Exp Neurol* 123: 204–215 (1993)

Grotta, J., "Safety and Tolerability of the Glutamate Antagonist CGS 19755 in Acute Stroke Patients," *Stroke* 25: 255 (1994)

Hargreaves, R. J., et al, "Competitive as well as uncompetitive NMDA receptor antagonists affect cortical neuronal morphology and cerebral glucose metabolism," *Neurochem Research* 18: 1263–1269 (1993)

Herrling, P. L. "D-CPPene (SDZ EAA 494), a competitive NMDA antagonist: Results from animal models and first results in humans," *Neuropsychopharmacology* 10, No 3S/Part 1: 591S (1994)

Horvath, Z. and Buzsaki, G, "MK-801-Induced Neuronal Damage in Normal Rats," *Soc Neurosci Abst* 19: 354 (1993)

Kristensen, et al, "The NMDA-receptor antagonist CPP abolishes neurogenic 'wind-up pain' after intrathecal administration in humans, *Pain* 51: 249–253 (1992)

Mao, J, et al, "Intrathecal MK-801 and local nerve anesthesia synergistically reduce nociceptive behaviors in rats with experimental peripheral mononeuropathy," *Brain Res.* 576: 254–262 (1992)

Marek, P., et al, "Excitatory amino acid antagonists (kynurenic acid and MK-801) attenuate the development of morphine tolerance in the rat," *Brain Research* 547: 77–81 (1991)

Massieu, L., et al, "A comparative analysis of the neuroprotective properties of competitive and uncompetitive N-methyl-D-aspartate receptor antagonists in vivo: implications for the process of excitotoxic degeneration and its therapy," *Neuroscience* 55: 883–92 (1993)

McCarthy, D. A., "History of the development of cataleptoid anesthetics of the phencyclidine type," pp. 17–23 in PCP (*Phencyclidine*): *Historical and Current Perspectives*, Domino, E. F., ed. (NPP Books, Ann Arbor, Mich., 1981)

Neugebauer, V., et al, "The clinically available NMDA receptor antagonist memantine is antinociceptive on rat spinal neurones," *NeuroReport* 4: 1259–1262 (1993)

Olney, J. W., "Glutamate," pp. 468–470 in *Encyclopedia of Neuroscience*, G. Adelman, ed. (Birkhauser, Boston, 1987 and 1995)

Olney, J. W., "Excitotoxicity and NMDA receptors," *Drug Dev Res* 17: 299–319 (1989a)

Olney, J. W., et al, "Pathological changes induced in cerebrocortical neurons by phencyclidine and related drugs," *Science* 244: 1360–1362 (1989b)

Olney, J. W., "Excitotoxic amino acids and neuropsychiatric disorders," pp 47–71 in *Annual Review of Pharmacology and Toxicology*, Volume 30, R. George, et al, eds. (Annual Reviews, Inc, Palo Alto, Calif., 1990)

Olney, J. W., et al, "NMDA antagonist neurotoxicity: Mechanism and prevention," *Science* 254: 1515–1518 (1991)

Olney, J. W. and Farber, N. B., "Efficacy of clozapine compared with other antipsychotics in preventing NMDA-antagonist neurotoxicity," *J Clin Psychiatry* 55(9) (suppl. B): 43–46 (1994)

Olney, J. W. and Farber, N. B., *Neuropsychopharmacology* (in press) (1995)

Seltzer, Z., et al, "Modulation of neuropathic pain behavior in rats by spinal disinhibition and NMDA receptor blockade of injury discharge," *Pain* 45: 69–75 (1991)

Sershen, H., et al, "Ibogaine reduces preference for cocaine consumption in C57BL/6By mice," *Pharmacol Biochem Behav* 47: 13–19 (1994)

Sheardown, M. J., et al, "Blockade of AMPA receptors in the CA1 region of the hippocampus prevents ischaemia induced cell death," pp. 245–253 in Krieglstein, J., and Oberpichler, H., eds., *Pharmacology of Cerebral Ischemia 1990* (Wissenschaftliche Verlagsgesellschaft, Stuttgart, Germany, 1990)

Tal, M. and Bennett, G. J., "Dextrorphan relieves neuropathic heat-evoked hyperalgesia in the rat," *Neuroscience Letters* 151: 107–110 (1993)

Tarnawa, L., et al, "GYKI 52466, an inhibitor of spinal reflexes, is a potent quisqualate antagonist," pp. 538–546 in Lubec and Rosenthal (eds.), *Amino Acids: Chemistry, Biology, and Medicine* (ESCOM Science Publishers, Leiden, Netherlands, 1990)

Trujillo, K. A. and Akil, H., "Inhibition of morphine tolerance and dependence by the NMDA receptor antagonist MK-801," *Science* 251: 85–87 (1991)

Woolf, C. J., "Recent advances in the pathophysiology of acute pain," *Br J Anaesth.* 63: 139–146 (1989)

Yamamoto, T. and Yaksh, T. L., "Spinal pharmacology of thermal hyperesthesia induced by constriction injury of sciatic nerve. Excitatory amino acid antagonists," *Pain* 49: 121–128 (1992)

I claim:

1. A method for reducing excitotoxic damage in a mammalian central nervous system, comprising administering, to a mammalian patient in need thereof, two drugs comprising:
   (a) a pharmacologically-acceptable NMDA receptor antagonist drug which penetrates mammalian blood-brain barriers in a quantity which is sufficient to therapeutically reduce excitotoxic damage to neurons if injected intravenously, but which also causes adverse neurotoxic or psychotomimetic side effects; and,
   (b) a pharmacologically-acceptable kainic acid receptor antagonist drug which penetrates mammalian blood-brain barriers and which suppresses activity at kainic acid-type glutamate receptors on neurons, in a quantity sufficient to inhibit the adverse neurotoxic or psychomimetic side effects that would be caused by the NMDA receptor antagonist drug in the absence of the kainic acid receptor antagonist drug.

2. The method according to claim 1 wherein the kainic acid receptor antagonist drug suppresses NMDA antagonist-induced adverse neurotoxic or psychomimetic side effects selected from the group consisting of: (a) formation of vacuoles in neurons in cerebrocortical or limbic brain regions; (b) expression of heat shock proteins in cerebrocortical or limbic brain regions; (c) alteration or loss of mitochondria in neurons; (d) neuronal death; and (e) hallucinations and other psychotomimetic effects that are associated with administration of NMDA receptor antagonist drugs.

3. The method according to claim 1 wherein the NMDA receptor antagonist drug is administered to the patient in order to reduce or prevent excitotoxic neuronal damage caused by an acute insult to the patient's central nervous system.

4. The method according to claim 1 wherein the NMDA receptor antagonist drug is administered to the patient in order to reduce or prevent neuronal damage associated with a progressive neurodegenerative disease.

5. The method according to claim 1 wherein the kainic acid receptor antagonist drug and the NMDA receptor antagonist drug are mixed together and administered in a single carrier.

6. The method according to claim 1 wherein the kainic acid receptor antagonist drug and the NMDA receptor antagonist drug are mixed together and administered in an essentially simultaneous manner.

7. The method according to claim 1 wherein the kainic acid receptor antagonist drug and the NMDA receptor antagonist drug are administered in a sequential manner which causes peak concentrations of the kainic acid receptor antagonist drug and the NMDA receptor antagonist drug in the blood to occur at different times.

8. In the method of administering an NMDA receptor antagonist drug to a patient in need thereof for a therapeutic purpose, the improvement wherein a pharmacologically acceptable kainic acid receptor antagonist drug which penetrates mammalian blood-brain barriers is also administered to the patient, in an amount effective in inhibiting adverse neurological effects that would be caused by the NMDA receptor antagonist drug in the absence of the kainic acid receptor antagonist drug.

9. The method according to claim 8 wherein the NMDA receptor antagonist drug is administered to the patient in order to reduce or prevent excitotoxic neuronal damage caused by an acute insult to the patient's central nervous system.

10. The method according to claim 8 wherein the NMDA receptor antagonist drug is administered to the patient in order to reduce or prevent neuronal damage associated with a progressive neurodegenerative disease.

11. The method according to claim 8 wherein the NMDA receptor antagonist drug is administered to the patient in order to reduce neuropathic pain.

12. The method according to claim 8 wherein the NMDA receptor antagonist drug is administered to the patient in order to suppress development of tolerance to a potentially addictive drug.

13. The method according to claim 8 wherein the kainic acid receptor antagonist drug and the NMDA receptor antagonist drug are mixed together and administered in a single carrier.

14. The method according to claim 8 wherein the kainic acid receptor antagonist drug and the NMDA receptor antagonist drug are mixed together and administered in an essentially simultaneous manner.

15. The method according to claim 8 wherein the kainic acid receptor antagonist drug and the NMDA receptor antagonist drug are administered in a sequential manner which causes peak concentrations of the kainic acid receptor antagonist drug and the NMDA receptor antagonist drug in the blood to occur at different times.

16. A pharmacological mixture comprising:
(a) a pharmacologically acceptable NMDA receptor antagonist drug which penetrates mammalian blood-brain barriers in a dosage which is therapeutically effective for human use; and,
(b) a pharmacologically acceptable kainic acid receptor antagonist drug which penetrates mammalian blood-brain barriers in an amount effective in inhibiting adverse neurological effects that would be caused by the NMDA receptor antagonist drug in the absence of the kainic acid receptor antagonist drug, in a pharmacologically acceptable carrier.

* * * * *